(12) United States Patent
Teng et al.

(10) Patent No.: US 6,767,561 B2
(45) Date of Patent: Jul. 27, 2004

(54) DNA POLYMERASE INHIBITORS, MIKANOLIDE AND DIHYDROMIKANOLIDE

(75) Inventors: Poon Beng Teng, Gif-sur-Yvette (FR); Marie-Christine Brezak Pannetier, Antony (FR); Mohamed Moumen, Sainte-Genevieve-des-Bois (FR); Gregoire Prevost, Antony (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 0 days.

(21) Appl. No.: 10/148,539

(22) PCT Filed: Nov. 30, 2000

(86) PCT No.: PCT/FR00/03337

§ 371 (c)(1), (2), (4) Date: Sep. 27, 2002

(87) PCT Pub. No.: WO01/39720

PCT Pub. Date: Jun. 7, 2001

(65) Prior Publication Data

US 2003/0118678 A1 Jun. 26, 2003

(30) Foreign Application Priority Data

Dec. 1, 1999 (FR) .......................................... 99 15126

(51) Int. Cl.[7] ............................................. A61K 35/78
(52) U.S. Cl. ....................................... 424/725; 424/774
(58) Field of Search .................................. 424/725, 774

(56) References Cited

PUBLICATIONS

Mathur et al. 1975. Revista Latinoamericana de Quimica. vol. 6(4), pp. 201–205, CAPLUS Abstract enclosed.*
Mathur et al. 1973. Phytochem. vol. 12(1), pp. 226–227, CAPLUS Abstract enclosed.*
Facey et al, "Investigations of . . . Derivatives", Abstracts of Papers of the National Meeting of the American Chemical Society, vol. 218, Aug. 1999, p. 294, XP000929986.
Ahmed, "Further . . . Cordata", Pharmazie, vol. 45, Sep. 1990, p. 697 XP002145554.
Facey et al, "Investigation . . . Activity", Journal of Pharmacyaand Pharmacology, London, GB, vol. 51,, 1999 pp. 1455–1460, XP000929990.
Zamorano et al, "Sesquiterpene . . . Ypacarayensis", Phytochemistry, vol. 38, 1995, pp. 1257–1260 XP000929993.

* cited by examiner

*Primary Examiner*—Christopher R. Tate
(74) *Attorney, Agent, or Firm*—Muserlian, Lucas and Mercanti

(57) ABSTRACT

The invention concerns DNA polymerase inhibitors, namely mikanolide and dihydromikanolide and dihydromikanolide-enriched extracts. Said compounds or mixtures can be used for preparing medicines designed to treat proliferative diseases, in particular cancer, viral diseases or parasitic diseases provoked by protozoae (for example malaria) or protists (for example, diseases caused by amoebae).

11 Claims, No Drawings

DNA POLYMERASE INHIBITORS, MIKANOLIDE AND DIHYDROMIKANOLIDE

This application is a 371 of PCT/FR00/03337 filed Nov. 30, 2000.

The present invention relates to, as medicaments and in particular as anti-proliferative, anti-viral and anti-parasitic agents, mikanolide, dihydromikanolide and dihydromikanolide enriched extracts. A subject of the invention is also obtaining them by extraction from the *Mikania micrantha* plant by a process described hereafter.

The plants have been a source of pharmaceutical products and ingredients in traditional medicine for a long time (Phillipson, J. D., *Trans. R. Soc. Trop. Med. Hyg.* (1994), 88 Suppl. 1, S17–S19). The medicaments formed by natural products or their synthetic analogues play a very important role.

For example, in oncology, products such as taxol (Paclitaxel®), vincristine (Oncovin®), vinorelbine (Navelbine®), teniposide (Vumon®), and several analogues of camptothecin (CPT) soluble in water (Pezzuto, J. M., *Biochem. Pharmacol.* (1997), 53, 121–133) are found. Other products originating from plants are moreover being studied for the prevention of the recurrence of stenosis.

In the field of cancer treatment, for example, camptothecin is a pentacyclic alkaloid isolated from *Camptotheca acuminata* wood (Wall, M. E., *Med. Res. Rev.* (1998), 18, 299–314). Initially, CPT was identified as an inhibitor of tumor proliferation in human cell models. Subsequently, the action mechanism of CPT has been identified as a topoisomerase I enzyme poison involved in the replication of DNA. An increasing number of CPT analogues (topotecan, CPT-11, BN-80915) are used in anti-cancer treatment in man (Lavergne, O. et al., *J. Med. Chem.* (1998), 41, 5410–5419).

Another example is taxol, a terpenic alkaloid isolated from *Taxus brevifolia*. Taxol is a powerful cytotoxin which inhibits tubulin, a protein involved in mitosis. This is a particularly effective product in ovarian cancer.

Moreover, the vinca alkaloids were first extracted from *Catharanthus roseus*. They were first used ethnobotanically for indications other than that of cancer treatment.

As far as the prevention of the recurrence of stenosis is concerned, studies indicate that it could be obtained thanks to a protein originating from *Saponaria officinalis*, saponin, recombinated with fibroblast growth factor (FGF). The latter allows targeting of the vascular cells due to its affinity for the FGF receptor (Lin P H et al., *Atherosclerosis* (April 1998), 137(2), 277–289).

The method for discovering such products is fractionation of plant extract molecules followed by the evaluation of their biological activities. But compared with the number of plant types, species and varieties, and the enormous quantity of molecules produced by these plants, the identification of a molecule and its biological activity remains a very difficult task to carry out.

*Mikania micrantha* is a plant which is pandemic in tropical regions. It proliferates in an extremely rapid fashion, to such an extent that it is nicknamed "a-mile-a-minute". *Mikania scandens* and *cordata* are often confused with it. These three species contain in particular mikanolide (I), dihydromikanolide (II), scandenolide (III) and dihydroscandenolide (IV).

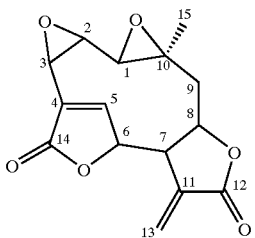

(I)

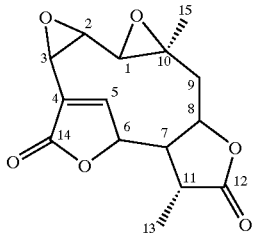

(II)

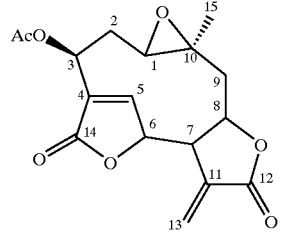

(III)

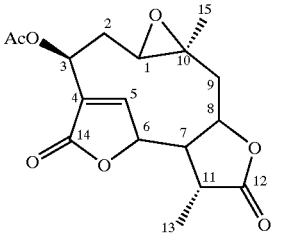

(IV)

Mikanolide, dihydromikanolide, scandenolide and dihydroscandenolide structures

The extraction of mikanolide, dihydromikanolide, scandenolide and dihydroscandenolide from *Mikania scandens*, *Mikania cordata* and *Mikania micrantha* was described in the following references respectively: Herz, *Tetrahedron Lett.* (1967), 32, 3111–15; Kiang, *Phytochemistry* (1968), 7(6), 1035–7; and Cuenca, *J. Nat. Prod.* (1988), 51(3), 625–6. The solvents used include chloroform and diethylether which cannot be used industrially because of their toxicity or inflammability.

Ethnobotanically, *Mikania scandens* and *cordata* have been and are still used by traditional medicine as an anti-asthmatic, analgesic, anti-rhumatic, anti-inflammatory, anti-cancer, febrifuge and vermifuge agent in Central America where its common name is Guaco. It is only in the last decade that some of these properties have been studied scientifically, in particular *Mikania cordata* extracts in the field of inflammation.

Recently, the Applicant has tested the anti-proliferative activity and found that, in a surprisingly, a dihydromikanolide and mikanolide enriched extract or pure forms of the latter have a powerful activity. In addition, dihydromikanolide and mikanolide inhibit the replication of DNA by inhibiting the DNA polymerase enzymes necessary for the multiplication of the eukaryotic and prokaryotic cells as well as viruses.

According to the invention, the said extract, obtained from *Mikania micrantha, Mikania scandens* and *Mikania cordata* leaves, comprises more than 50%, and preferably more than 60% mikanolide and dihydromikanolide. Even more preferably, said extract comprises more than 70% mikanolide and dihydromikanolide. Preferably, said extract comprises moreover less than 10%, and more preferably less than 5%, scandenolide and dihydroscandenolide. Furthermore, extracts comprising more than 20% dihydromikanolide, and more preferably, more than 30% dihydromikanolide are also preferred.

The said extract can be prepared according to the extraction method described hereafter starting from *Mikania micrantha*, without however excluding the species *Mikania scandens* and *Mikania cordata*.

A subject of the invention is therefore firstly a process for the preparation of an extract according to the invention, characterized in that it comprises the following successive stages:

grinding up and drying of *Mikania micrantha, Mikania scandens* and *Mikania cordata* leaves;

addition of a solvent chosen from toluene, ethyl acetate, toluene and ethyl acetate mixtures, toluene and acetone mixtures, ethyl acetate and heptane mixtures, and heptane and acetone mixtures in proportions of 7:3 to 3:7 to the ground leaves of *Mikania micrantha, Mikania scandens* and *Mikania cordata;* filtration and recovery of the filtrate;

concentration of the extract of the primary extract solution in order to obtain a concentration of 2.5 to 10% in dry extract;

dividing the concentrated extract obtained in the preceding stage between the extraction solvent and a mixture comprising 10% to 50% methanol or ethanol in water;

washing the alcohol-water phase with n-hexane or heptane;

elimination of the alcohol of the alcohol-water phase;

extraction of the aqueous phase obtained with ethyl acetate;

drying of the ethyl acetate phase with a drying agent;

evaporation of the solvents and recovery of the dry extract;

purification of the dry extract obtained by a physico-chemical separation method; and obtaining, after drying, a dry extract according to the invention.

According to the invention, the physico-chemical separation method can be, for example, filtration on silica gel, or also, according to a preferred variant, crystallization from methanol, ethanol or acetone.

If filtration on silica gel is chosen, the eluents used are preferably heptane-ethyl acetate mixtures in proportions comprised between 9:1 and 1:1.

In the case where crystallization is chosen, it is preferably carried out at a temperature comprised between −10 and 5° C. for a duration preferably comprised between 2 and 16 hours.

Moreover, according to a preferred variant of the above process, dividing the concentrated extract is carried out using a mixture comprising 25 to 30% methanol in water. Preferably, the lower aqueous phase will be heated to facilitate phase separation, for example at a temperature of 30 to 50° C.

The dry extract as obtained by the above process can be dihydromikanolide-enriched by conversion of the mikanolide to dihydromikanolide by catalytic hydrogenation. Subsequently, re-crystallization allows the pure compound to be obtained.

A subject of the invention is also therefore a process for the preparation of a dihydromikanolide-enriched extract characterized in that it consists of hydrogenation of the dry extract described previously, dissolved in ethyl acetate, at a temperature comprised between 10 and 35° C., in the presence of a hydrogenation catalyst under a pressure of 1 to 2 hydrogen atmospheres for a duration preferably comprised between 4 and 16 hours. Preferably, the hydrogenation catalyst is $Pd/CaCO_3$.

A subject of the invention is in addition a dry extract highly enriched with dihydromikanolide as obtained by the hydrogenation process described previously followed by evaporation of the reaction solvents after elimination of the catalyst by filtration, the said dry extract being characterized in that it comprises at least 50% dihydromikanolide, and preferably at least 92% dihydromikanolide (pharmaceutical quality).

According to the invention, after hydrogenation, dihydromikanolide can be obtained directly by adding a liquid n-alkane to the dihydromikanolide enriched extract in solution in ethyl acetate and recovery of said dihydromikanolide by filtration. Preferably, the n-alkane used in order to obtain crystallization is n-hexane or n-heptane, and more preferably n-heptane.

The process described above has the advantage of being able to obtain dihydromikanolide at a degree of purity greater than 92%, without necessarily needing to resort to a chromatographic type separation.

The different processes described above as well as other possible variants are described in detail in the part entitled "Preparation of the products of the invention".

Thus the Applicant has just found that mikanolide, dihydromikanolide and the different extracts of the invention, have significant pharmacological properties, in particular as anti-proliferative agents (and in particular as an anti-cancer agent), as anti-viral agents or as anti-parasitic agents. These properties are illustrated in the part entitled "Pharmacological study of the products of the invention".

A subject of the invention is also therefore, as a medicament, a dihydromikanolide enriched extract as described previously or dihydromikanolide. A particular subject of the invention is the use of an extract as described previously, of mikanolide or dihydromikanolide for preparing a medicament intended to inhibit the DNA polymerases. In particular, a subject of the invention is the use of an extract as described previously, of mikanolide or dihydromikanolide for preparing a medicament intended to treat proliferative diseases, and in particular cancer, as well as viral diseases and parasitic diseases caused by protozoa (for example malaria) or protists (for example diseases caused by amoeba). A subject of the invention is in addition a pharmaceutical composition comprising a dihydromikanolide-enriched extract as described previously or dihydromikanolide as active ingredient, with optionally one or more pharmaceutically acceptable excipients.

For the uses according to the invention, dihydromikanolide or a dihydromikanolide-enriched extract is preferred. More preferentially, dihydromikanolide is chosen for the uses according to the invention.

The pharmaceutical composition according to the invention can be in the form of a solid, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing dihydromikanolide can also be presented in liquid form, for example, solutions, emulsions, suspensions or syrups. Appropriate liquid supports can be, for example, water, organic solvents such as glycerol or glycols, as well as their mixtures, in varying proportions, in water.

The administration of a medicament according to the invention can be carried out by topical, oral, parenteral route, by intramuscular injection, etc.

The administration dose envisaged for a medicament according to the invention is comprised between 0.1 mg to 10 g according to the type of active compound used.

Preparation of the Products of the Invention

The following solvents can be used for the primary extraction:

group I: toluene, ethyl acetate, toluene and ethyl acetate mixtures, toluene and acetone mixtures, ethyl acetate and heptane mixtures, and heptane and acetone mixtures in proportions of 7:3 to 3:7 and preferably in 1:1 mixture (proportions expressed as volume for volume);

group II: acetone, ethanol and methanol;

group III: acetone and water, ethanol and water or methanol and water mixtures in proportions of 9:1 to 1:1 (proportions expressed as volume for volume, as in the rest of the present text, except where indicated otherwise).

Preferably, the solvent used in the first phase of extraction is ethyl acetate.

According to the invention, the primary extract is divided into a mixture comprising 10% to 50% methanol or ethanol in water, and preferably in a mixture comprising 25% to 40% methanol in water at a temperature preferably comprised between 15 and 50° C. Preferably, the lower aqueous phase is heated, for example at a temperature comprised between 30 and 50° C., in order to obtain a more distinct phase separation.

In the case where primary extraction is carried out using a solvent or mixture of solvents of group I, the division is preceded by concentration of the primary extract solution in order to obtain a concentration of 2.5 to 10% of dry extract.

In the case where primary extraction is carried out using a group II solvent, before division of the primary extract, concentration of the solution of primary extract is carried out in order to obtain a concentration of approximately 50% of dry extract followed by dissolving the concentrated extract in order to obtain a dilute extract containing from 2.5 to 10% of dry extract, said dissolution being carried out using a solvent or a mixture of solvents of group I, and preferably in ethyl acetate.

In the case where primary extraction is carried out using a group III solvent, before division of the primary extract, evaporation of the primary extract solution is carried out in order to obtain a concentration of 5 to 25% of dry extract, this eliminates the solvents which are miscible with water. Extraction is then carried out using a solvent or mixture of solvents of group I, preferably ethyl acetate.

Once division of the primary extract has been carried out (which has optionally undergone the previous operations described above), the alcohol-water phase is washed with n-hexane or heptane, and preferably with heptane, so as to eliminate the chlorophylls, sterols and other vegetable lipids.

The alcohol of the alcohol-water phase is eliminated by evaporation and a new extraction of the resulting aqueous phase is carried out using ethyl acetate.

The ethyl acetate phase is then dried with a drying agent such as anhydrous $MgSO_4$ or $Na_2SO_4$, filtered and evaporated to dryness.

The resulting dry extract of the previous stage can be purified by filtration, for example by filtration on silica gel using a load comprised of 2 to 20%, preferably approximately 5%, in eluent with heptane-ethyl acetate mixtures in proportions comprised between 8:2 and 1:1, preferably 7:3, or with toluene-acetone mixtures in proportions comprised between 9:1 and 6:4, preferably 7:3. The filtrate is concentrated to dryness in order to obtain, according to the invention, a mikanolide and dihydromikanolide-enriched extract.

Alternatively, the dry extract can be purified by crystallization from methanol, ethanol or acetone, for example from a methanolic solution comprising a concentration of dry extract of the order of 10%, the mixture being left to rest for a duration preferably comprised between 12 and 16 hours at a temperature preferably comprised between −10 and 5° C. After filtration (or centrifugation), rinsing the crystals with a little methanol and drying, a mikanolide and dihydromikanolide-enriched extract is obtained.

In order to convert the mikanolide to dihydromikanolide, a hydrogenation stage can be carried out, for example by dissolving the extract obtained previously in ethyl acetate at a temperature preferably comprised between 10 and 35° C. in the presence of a catalyst such as $Pd/CaCO_3$ at 5% under a pressure of 1 to 2 hydrogen atmospheres. This hydrogenation stage moreover has the advantage of facilitating the purification of the mixture constituted by the mikanolide and dihydromikanolide enriched extract.

Crystallization of the dihydromikanolide from the concentrated solution in ethyl acetate is then carried out by adding a liquid n-alkane, for example n-heptane or n-hexane, and preferably n-heptane. Dihydromikanolide with a degree of purity at least equal to 92% is then obtained.

Unless otherwise specified, all the technical and scientific terms used here have the same meaning as that usually understood by an ordinary specialist in the field to which this invention belongs. Similarly, all the publications, patent applications, all the patents and all other references mentioned here are incorporated by way of reference.

The following examples are presented in order to illustrate the above procedures and should in no way be considered as a limit to the scope of the invention.

EXAMPLES

Example 1

100 g of dry (containing less than 10% moisture) *Mikania micrantha* leaves (with their stems), harvested between May and July in the region around Sungei Ara, Penang (Malaisia) are ground in a grinder in order to produce particles of a size less than 4 mm. After the addition of 1 liter of ethyl acetate, the mixture is stirred vigorously for 30 minutes at a temperature of 55 to 60° C. The solid residue is separated by filtration and subjected to a second extraction under the same conditions. The extracts of the first and second extraction stages are combined. The extract is concentrated under reduced pressure in order to obtain a concentration of solid content of approximately 5%, which corresponds to a volume of approximately 110 ml. 40 ml of n-heptane is then added.

125 ml of a methanol-water mixture 1:2 is added to the extract and stirred vigorously in a separating funnel then left to settle. The lower aqueous phase is heated to approximately 40–50° C. to break down the possible emulsions and to facilitate phase separation. The water-methanol phase is withdrawn from below. The division is repeated twice more by using 50 ml of a methanol-water mixture 1:3 each time.

20 ml of n-heptane is then added to the methanol-water solution. After vigorous stirring in a separating funnel, the two phases are left to separate. The degreased methanol-water solution is then withdrawn from below.

The methanol-water solution is then concentrated under reduced pressure in order to eliminate the methanol and obtain an aqueous suspension.

100 ml of ethyl acetate and 15 g of sodium chloride are added to the aqueous suspension. The mixture is stirred vigorously in a separating funnel then allowed to settle. The liquid-liquid extraction is repeated once with 50 ml of ethyl acetate.

The combined ethyl acetate extracts are dried by adding approximately 30 g $MgSO_4$, the mixture being stirred for approximately 10–20 minutes before being filtered (the $MgSO_4$ being rinsed with twice 25 ml of ethyl acetate). The filtrate and the ethyl acetate having been used in the rinsing, combined, are then evaporated to dryness under reduced pressure.

The solid extract obtained is then dissolved in 5 ml MeOH and allowed to crystallize at 4° C. for 16 hours. Filtration is then carried out on frit, the crystals recovered are rinsed with 2 ml MeOH at 4° C. After drying in a vacuum oven, 481.2 mg of dry extract is obtained.

Analysis by HPLC of the dry extract obtained produces the following results:

| Compound | Proportion by weight |
| --- | --- |
| Mikanolide | 68.0% |
| Dihydromikanolide | 25% |
| Scandenolide | 5% |

Example 2

The same process as that of Example 1 is used at the start. However, instead of adding 5 ml MeOH after drying with $MgSO_4$ and carrying out crystallization, 2.8 g of celite is added and the solvents are evaporated to dryness. Filtration is then carried out on a silica bed (12 g $SiO_2$ 35–70 μm). 26 ml (i.e. four times the column volume) of heptane/ethyl acetate mixture 2:8 (the corresponding fractions being eliminated) is passed through 4 times, then 26 ml of heptane/ethyl acetate mixture 6:4 (the corresponding fractions being recovered) is passed through 14 times. The fractions recovered are combined and evaporated to dryness in order to obtain the final dry extract.

Example 3

330 mg of dry extract as obtained in Example 1 is dissolved in 80 ml of ethyl acetate and the solution, to which is added 248 mg of $Pd/CaCO_3$ at 5%, is placed under a current of hydrogen (pressure comprised between 1 and 2 atmospheres). The agitation and the hydrogen flux are maintained overnight and the completion of the reaction is monitored by HPLC chromatography. Once the reaction is completed, 1 g of celite is added and stirring is carried out for 10 minutes. 5 g of anhydrous $MgSO_4$ is then added and the solids are eliminated by filtration on celite. The celite is rinsed with twice 10 ml of ethyl acetate, then the solvents are eliminated by evaporating to dryness. 3 ml of acetone then 3 ml of heptane are added to the recovered solid. The solvents are partially evaporated with a rotary evaporator at 50° C. then cooled down to 0° C. using an ice bath. After filtration, the solid is rinsed with twice 1 ml of a 50/50 acetone/heptane mixture. Evaporation is then carried out to dryness and 214 mg of dihydromikanolide is recovered.

NMR $^1$H (DMSO d6, 400 MHz, δ): 0.96 (s, 3H); 1.25–1.27 (d, 3H); 1.84–1.89 (m, 1H); 2.04–2.10 (m, 1H); 2.49–2.50 (t, 1H); 2.93–2.98 (m, 1H); 3.19 (s, 1H); 3.38–3.39 (d, 1H); 3.98–3.99 (d, 1H); 4.62–4.68 (m, 1H); 5.42–5.43 (d, 1H); 7.61–7.62 (d, 1H). NMR $^{13}$C (DMSO d6, δ): 13.3; 20.9; 39.7; 41.1; 42.3; 50.3; 52.3; 54.9; 57.5; 76.7; 81.8; 128.7; 149.9; 171.1; 176.1.

Pharmacological Study of the Products of the Invention

By way of an example, the effects of a treatment with the compounds of the invention will be studied on:

the incorporation of cytosine labelled with $^{32}$P in a DNA in the presence of DNA polymerase (acellular system);

the incorporation of tritiated thymidine in the DNA of tumor cells in division over a short period (cell system);

the proliferation of two human cell lines Mia-Paca2 and DU145.

1) Procedures

Cell Lines

The cell lines DU145 (human prostate cancer cells), HT29 (cancer of the colon) and Mia-PaCa2 (human pancreatic cancer cells) were acquired from the American Tissue Culture Collection (Rockville, Md., USA).

Incorporation of Cytosine Labelled With $^{32}$P into a DNA in the Presence of DNA Polymerase in an Acellular System Labelling of the DNA is carried out on a DNA fragment which incorporates nucleotides by way of the activity of the DNA polymerase enzyme. From these nucleotides, the dCTP is labelled by radioactive phosphorus ($^{32}$P).

Plasmidic DNA (pc DNA 3, invitrogen, Netherlands) is diluted to a concentration of 2 ng in 45 μl of TE solution (10 MM Tris-HCl; pH 8.0; 1 mM EDTA) then denatured by heating at 100° C. for 10 minutes before being replaced directly in ice. The denatured DNA is placed in the tube which contains the buffer solution of dATP, dGTP, dTTP, the Klenow DNA polymerase enzyme without exonuclease and the random primers (Rediprime II random prime labelling system, RPN 1633, RPN 1634, Amersham pharmacia biotech). 2 μl of Redivue [$^{32}$P]dCTP (1-deoxycytidine 5'(α-$^{32}$P), specific activity 250 μCi, Amersham), is added to start the reaction. The reaction is carried out in the presence or absence of the compound to be tested for 10 minutes at 37° C. or 1 hour at ambient temperature. The reaction is stopped by adding 5 μl of 0.2 M EDTA. To recover the DNA, 200 μl of isopropanol is added and the pellet of DNA is recovered after centrifugation for 10 minutes at 12 000 r.p.m. then washed with 70% ethanol. After complete drying in ambient air, the DNA is solubilized in 50 μl of TE. 10 μl is counted into 5 ml of scintillor (Instagel® plus and Packard scintillation counter). The results are expressed as a percentage of the inhibition of incorporation of the labelled nucleotide in the sample with respect to the control (100–(DPM of the sample/DPM control)*100).

Incorporation of Thymidine Labelled With Tritium into DNA Cells in Exponential Growth Phase (in vitro)

HT29 cells are seeded in 96-well plates (culturPlate-96, Packard; 4000 cells per well) with the medium (DMEM, Gibco BRL complemented with 10% foetal calf serum, Gibco BRL). On day 3, the medium is removed and replaced by medium containing the tritiated thymidine (5'-thymidine TRK.328, 1 mCi, 0.6 μCi/wells, Amersham) with or without the products (range of 100 to 0.19 μg/ml per ½ dilutions).

The treatments are carried out for 1 hour. The medium is then removed and the cells are washed twice with 200 µl of PBS (Gibco BRL). The lysis solution (SDS 1.25%; EDTA 5 mM) is added and left for 10 minutes at ambient temperature, then 75 µl of scintillating liquid (microscint® 40, Packard) is added. Reading is carried out using Topcount® (Packard). The results are expressed as a percentage of the inhibition of incorporation of the labelled nucleotide in the sample with respect to the control (100−(DPM of the sample/DPM control)*100).

Cell Proliferation Tests

The cells placed in 80 µl of Dulbecco's modified Eagle medium (Gibco-Brl, Cergy-Pontoise, France) completed with 10% foetal calf serum inactivated by heating (Gibco-Brl, Cergy-Pontoise, France), 50000 units/l of penicillin and 50 mg/l streptomycin (Gibco-Brl, Cergy-Pontoise, France), and 2 mM of glutamine (Gibco-Brl, Cergy-Pontoise, France) were seeded on a 96-well plate on day 0. The cells were treated on day 1 for 96 hours with increasing concentrations of each of the compounds to be tested at 50 µg/ml. At the end of this period, quantification of cell proliferation is evaluated by a colorimetric test based on the cleavage of the tetrazolium salt WST1 by mitochondrial dehydrogenases in viable cells leading to the formation of formazan (Boehringer Mannheim, Meylan, France). These tests are carried out in duplicate with 8 determinations per concentration tested. For each compound to be tested, the values included in the linear part of the sigmoid were retained for linear regression analysis and used to estimate the inhibitory concentration $IC_{50}$. The products are solubilized in dimethylsulphoxide (DMSO) at $10^{-2}$ M and finally used in culture with 0.5% DMSO.

2) Results:

The results of the inhibition tests of the DNA polymerase activity are given in table I below:

TABLE I

Inhibition of the DNA polymerase activity by dihydromikanolide and mikanolide (100 µg/ml) in an acellular system

| Compound | Inhibition of incorporation (%) |
|---|---|
| Dihydromikanolide | 73 (n = 5; standard deviation σ = 7) |
| Mikanolide | 79.6 (n = 3; standard deviation σ = 11.0) |

The incorporation of tritiated thymidine into the DNA of HT29 human cells is inhibited when the latter are treated by dihydromikanolide and mikanolide (cf. Table II hereafter).

TABLE II

Inhibition of incorporation (dpm sample/dpm control)

| Concentration (µg/ml) | 100 | 50 | 25 |
|---|---|---|---|
| Dihydromikanolide | 0.19 | 0.29 | 0.58 |
| Mikanolide | 0.53 | 0.61 | 1.04 |

Finally, in Table III below the values in vitro of the activities of proliferation inhibition with respect to DU145 and Mia-Paca2 human tumor cells treated by mikanolide and the compounds of Examples 1 and 2.

TABLE III

Inhibition of the proliferation human tumor cells treated with mikanolide and the compounds of Examples 1 and 2.

| | Inhibitory concentration $IC_{50}$ (µM) | |
|---|---|---|
| Compound | Mia-Paca2 | DU-145 |
| Mikanolide | 3 | 15 |
| Example 1 | 1.6 | 4.6 |
| Example 2 | 1.3 | 4.3 |

What is claimed is:

1. A process for obtaining a dry extract of *Mikania micrantha, Mikania scandens* and *Mikania cordata* leaves, comprising at least 50% by weight of mikanolide and dihydromikanolide and at least 20% dihydromikanolide, comprising grinding and drying *Mikania micrantha, Mikania scandens* and *Mikania cordata* leaves;

adding to the ground leaves of *Mikania micrantha, Mikania scandens* and *Mikania cordata* leaves, a solvent selected from the group consisting of toluene, ethyl acetate, toluene and ethyl acetate mixtures, toluene and acetone mixtures, ethyl acetate and heptane mixtures, and heptane and acetone of the mixtures in proportions of 7:3 to 3:7;

filtering the mixture and recovering the filtrate;

concentrating the filtrate of the primary extract solution to obtain a concentration of 2.5 to 10% dry extract;

dividing of the concentrated extract obtained in the preceding stage between the extraction solvent and a mixture comprising from 10% to 50% methanol or ethanol in water;

washing of the alcohol-water phase with n-hexane or heptane;

eliminating the alcohol of the alcohol-water phase;

extracting the aqueous phase obtained with ethyl acetate;

drying of the ethyl acetate phase with a drying agent;

evaporating the solvents and recovering the dry extract;

purifying the dry extract obtained by a physico-chemical separation method;

obtaining, after elimination of the solvents, the desired extract.

2. The process of claim 1 wherein the division of the concentrated extract is carried out using a mixture comprising from 25 to 30% methanol in water.

3. The process of claim 1 wherein the physico-chemical separation method is crystallization from methanol, ethanol or acetone.

4. The process of claim 1 wherein the physico-chemical separation method is filtration on silica gel.

5. A process for the preparation, from a dry extract of *Mikania micrantha, Mikania scandens* and *Mikania cordata* leaves comprising at least 50% by weight of mikanolide and dihydromikanolide and at least 20% dihydromikanolide, of a dihydromikanolide-enriched extract comprising grinding and drying *Mikania micrantha, Mikania scandens* and *Mikania cordata* leaves;

adding to the ground leaves of *Mikania micrantha, Mikania scandens* and *Mikania cordata* leaves, a solvent selected from the group consisting of toluene, ethyl acetate, toluene and ethyl acetate mixtures, toluene and acetone mixtures, ethyl acetate and heptane mixtures, and heptane and acetone of the mixtures in proportions of 7:3 to 3:7;

filtering the mixture and recovering the filtrate;

concentrating the filtrate of the primary extract solution to obtain a concentration of 2.5 to 10% dry extract;

dividing of the concentrated extract obtained in the preceding stage between the extraction solvent and a mixture comprising from 10% to 50% methanol or ethanol in water;

washing of the alcohol-water phase with n-hexane or heptane;

eliminating the alcohol of the alcohol-water phase;

extracting the aqueous phase obtained with ethyl acetate;

drying of the ethyl acetate phase with a drying agent;

evaporating the solvents and recovering the dry extract;

purifying the dry extract obtained by a physico-chemical separation method;

obtaining, after elimination of the solvents, the desired extract, hydrogenating the said extract dissolved in ethyl acetate at a temperature of 10 to 350° C., in the presence of a hydrogenation catalyst under a pressure of 1 to 2 hydrogen atmospheres.

6. A process for preparation of dihydromikanolide containing at least 50% by weight of mikanolide and dihydromikanolide and at least 20% dihydromikanolide comprising crystallizing dihydromikanolide by adding a liquid n-alkane to the of dihydromikanolide-enriched ethyl acetate extract of claim 5 and recovery of said dihydromikanolide by filtration.

7. The process of claim 6 wherein the alkane is n-heptane or n-hexane.

8. The process of claim 6 wherein the alkane is n-heptane.

9. A composition for treating cancer comprising an amount of the extract obtained by the process of claim 1 sufficient to treat cancer and a pharmaceutical carrier.

10. A composition for treating cancer comprising an amount of the extract obtained by the process of claim 5 sufficient to treat cancer and a pharmaceutical carrier.

11. A method of treating cancer in warm-blooded animals comprising administering to warm-blooded animals in need thereof an amount of a composition obtained by the process of claim 1 sufficient to treat cancer.

* * * * *